United States Patent [19]

Marrelli et al.

[11] Patent Number: 5,625,293

[45] Date of Patent: Apr. 29, 1997

[54] DETERMINATION OF THE WATERCUT OF A MULTIPHASE FLOW DIRECTLY FROM MEASURED MICROWAVE FREQUENCY DIELECTRIC PROPERTIES

[76] Inventors: John D. Marrelli; Joseph D. Stafford, both of P.O. Box 770070, Houston, Tex. 77217-0070; David A. Helms, 6223 Braesheather, Houston, Tex. 77096; Michael G. Durrett, 9010 Railton, Houston, Tex. 77080; Gregory J. Hatton, 3207 Rambling Creek, Kingwood, Tex. 77345

[21] Appl. No.: 431,873

[22] Filed: May 1, 1995

[51] Int. Cl.$^6$ .................................................. G01N 22/00
[52] U.S. Cl. ............................ 324/638; 324/640; 324/84; 73/61.41
[58] Field of Search ............................... 324/638, 639, 324/640, 634, 84

[56] References Cited

U.S. PATENT DOCUMENTS

| | | |
|---|---|---|
| 4,507,602 | 3/1985 | Aguirre .................... 324/638 |
| 4,902,961 | 2/1990 | De ............................ 324/640 |
| 5,144,224 | 9/1992 | Larsen ...................... 324/638 |
| 5,331,284 | 7/1994 | Jean ......................... 324/639 |

*Primary Examiner*—Kenneth A. Wieder
*Assistant Examiner*—Jose M. Solis
*Attorney, Agent, or Firm*—Henry H. Gibson; Harold J. Delhommer; James L. Bailey

[57] ABSTRACT

The watercut of fluid in a mulitphase flow is measured. Microwave energy in the 10 Ghz range is transmitted through a test call having flow passing therein through a known geometry. Attenuation and phase shift of the microwave energy is measured and used to derive the wave number of the microwaves in the unknown fluid. The water fraction of the unknown fluid is then determined from the wave number and the known geometry of the test all using Hannai's equation.

10 Claims, 1 Drawing Sheet

DETERMINATION OF THE WATERCUT OF A MULTIPHASE FLOW DIRECTLY FROM MEASURED MICROWAVE FREQUENCY DIELECTRIC PROPERTIES

BACKGROUND OF THE INVENTION

This invention relates to the monitoring or measuring of the water cut or percentage of water present in produced fluids from a well borehole. More particularly, the invention relates to the use of microwave energy to measure the dielectric properties of multiphase fluids containing oil, water, gas and possibly entrained solids in a producing well, and the use of such measured dielectric properties to determine the water cut of the produced fluid directly.

A prior art co-assigned patent (U.S. Pat. No. 4,947,128) discloses a device and method for using microwave energy to measure the water cut of a petroleum stream based on the relative phase and the intensity of reflected and transmitted microwave energy impinging upon the petroleum stream. In this co-variance water cut monitoring scheme, however, for simplification of analysis certain assumptions are made. One critical assumption, used in the mini-computer program in the device, is that the continuous phase (i.e. oil continuous or water continuous) of the multiphase fluid flow is known. A priori knowledge of this parameter is not always possible and, even if initially known accurately, can change during the time period of the measurements themselves. Moreover it has been determined that other unknown variables can affect this measurement process such as temperature changes, changes in water salinity and changes in the type and quantity of solid impurities in the monitored production fluid stream.

BRIEF DESCRIPTION OF THE INVENTION

In the methods of measurement of the present invention, no assumption is made of a priori knowledge of the continuous phase of the production fluid. The measurement technique is again based on the use of microwave frequency electromagnetic energy allowed to impinge upon the production fluid stream. Continuous wave microwave energy at a frequency of approximately 10 gigahertz is directed through the flowing production fluid in a test cell having a window which is essentially transparent to the microwave energy. The intensity of the microwave energy transmitted through the test cell and the intensity of the microwave energy reflected from the test cell as microwave energy passes through the test cell in two directions is measured. These measurements are used to determine the so called "S-Parameters" of the test cell dielectric material. From these S-Parameters, an analysis mini-computer determines $\Gamma$, the reflection coefficient and T, the transmission coefficient of the test cell material. From these T and $\Gamma$ parameters the analysis computer is programmed to determine the phase shift parameter n, the wave number $\kappa_u$ is known, then $\epsilon_u$, the dielectric constant of the unknown fluid may be determined from known relationships. Once $\epsilon_u$ is known, the water cut fraction f may be found from equations for the particular geometry of the test cell, such as Hanai's equations.

The invention may best be understood from the following detailed description thereof when taken in conjunction with the appended drawings. It will be understood that the appended drawings are intended as illustrative only and not as limitative of the invention.

DESCRIPTION OF THE PREFERRED EMBODIMENT

The present invention discloses a method whereby the water cut of production fluid from a producing well, or the like, can be determined directly from the dielectric properties of the oil/water mixture. Methods according to the concepts of the present invention are preferred over previous methods which require a priori determination of the continuous phase of the fluid flow prior to the water cut or water fraction determination for a number of reasons. Among these reasons are that the a priori determination of the continuous phase may be erroneous when made, or even if correctly made, can change under field production conditions. Changes of the water salinity or wide temperature changes and the effect of solid or other impurities in the production fluid can lead to such a change from water continuous phase (oil droplets emulsified in water) to oil continuous phase (water droplets emulsified in oil).

The methods of the present invention call for directing microwave electromagnetic energy through a flowing stream of production fluid. Continuous wave microwave measurements are contemplated although each individual continuous wave measurement may be separated, perhaps at intervals of less than one second each. In fact, repetition rates of several hundred per second can be used, still applying the principles of the present invention for continuous wave measurements.

Figure 1:
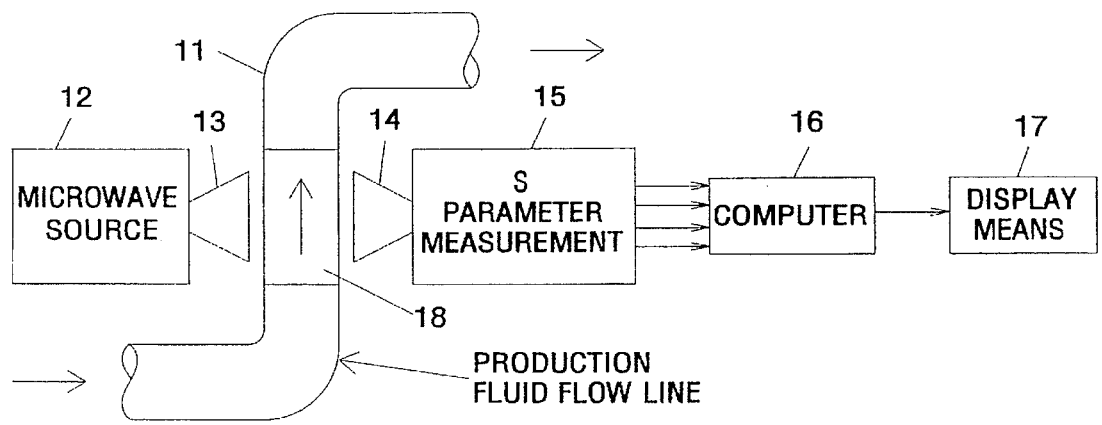
FIG. 1 shows schematically the overall layout of a measurement system for analyzing production fluid flow according to the concepts of the invention.

Referring initially to FIG. 1 a system employing the concepts of the present invention is shown schematically. A microwave source 12 directs approximately 10 gigahertz microwave frequency electromagnetic energy through a microwave transparent portion 18 of a fluid flow line 11 which contains flowing fluids from a producing well. It is desirable to be able to measure the dielectric properties of the flowing fluid and from these to be able to deduce the water cut or water fraction f of the flowing production fluid in line 11. The microwave transparent window 18 in pipe 11 is composed of a section of fiberglass or thermoplastic material, ceramic or the like having a negligible attenuation for microwaves in the 10 gigahertz frequency range.

As will be discussed in more detail subsequently, microwave energy is transmitted via a horn antenna 13 through the fluid flowing through window 18 and is received at antenna 14. An S-parameter measuring circuitry 15 (shown in more detail in FIG. 2) detects transmitted and reflected microwave energy present at antennas 13 and 14 and forms ratios known as the S-Parameters of these measurements. The measured S-Parameters are supplied to minicomputer 16 which is programmed in accordance with the description to follow in more detail, for determining $\Gamma$ the reflection coefficient, T the transmission coefficient and, from there the phase parameter n and $\kappa_u$, the wave number of the interviewing material flowing between the antennas 13 and 14. Once the wave number $\kappa_u$ of the sample is known then the water cut fraction is easily determinable from, for example Hannai's equation. The water cut, dielectric properties and other parameters, determined by the programmed computer 16, may then be conveniently displayed on a display means 17 which may comprise a laser printer, a Cathode Ray Tube display or other form of record medium as desired.

Figure 2:
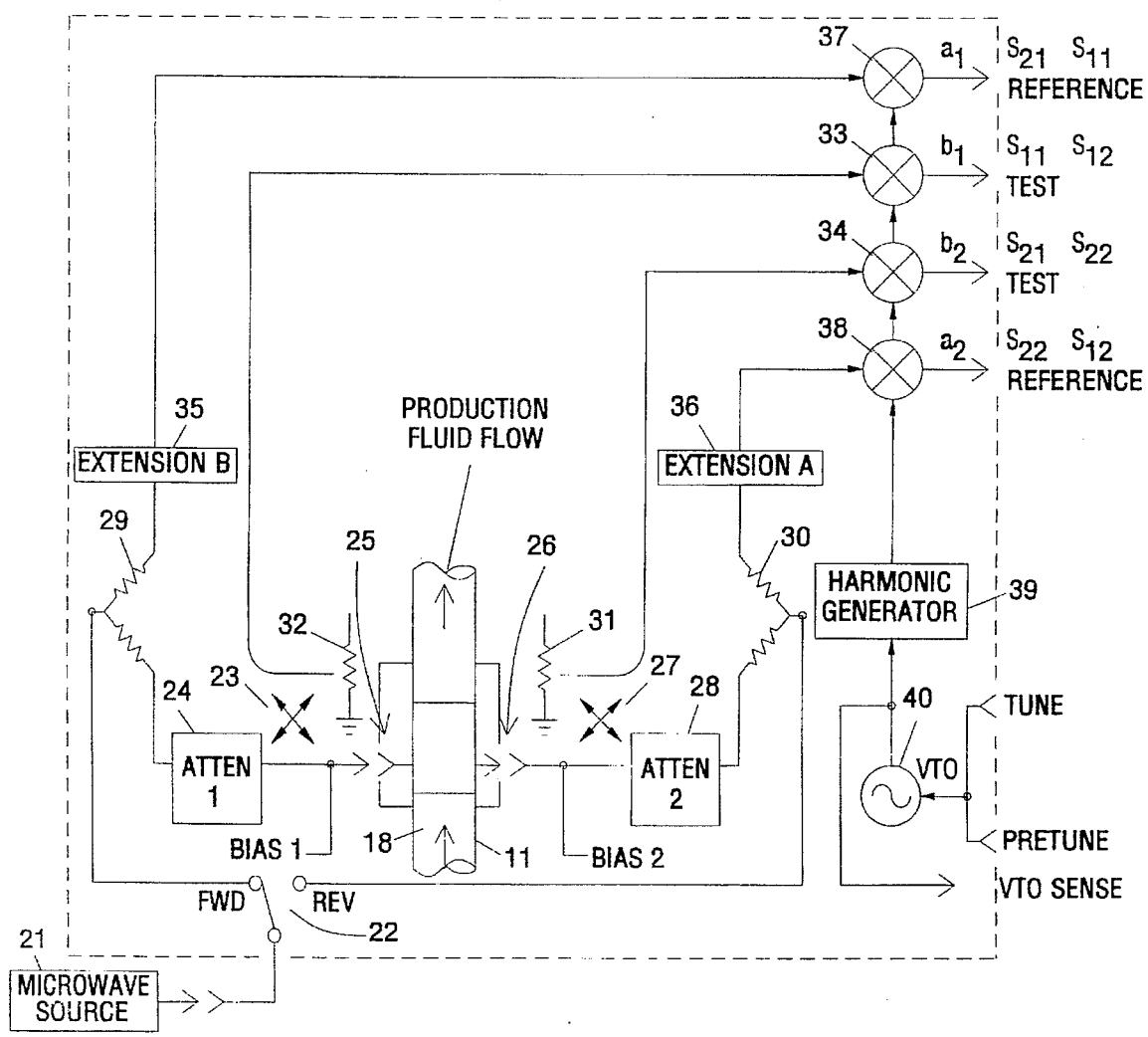
FIG. 2 shows schematically a portion of the system of FIG. 1 for measuring the S parameters of the flowing fluid.

Referring now to FIG. 2, the S-Parameter measurement circuitry of FIG. 1 is shown in more detail, but still schematically. Microwave energy from, for example, a Gunn diode source 21 at a frequency of about 10 gigahertz is supplied via a reversing switch 22 to an antenna 25 directly via splitter 29 and attenuator 24. A portion of the supplied microwave energy is supplied via splitter 29 and a line extension 35 to frequency conversion mixer 37 as a reference signal denoted $a_1$ in FIG. 2. With switch 22 in the position shown, antenna 25 radiates the microwave energy through the window 18 in flow line 11 and a portion of it is received at antenna 26. Reflected microwave energy is received back at antenna 25 and is prevented by circulator 23 from going back to splitter 29. Instead the reflected energy at antenna 25 is routed via detector 32 to frequency conversion mixer 33 where its frequency is translated to that of the output signal which is denoted as $b_1$ in FIG. 2. The transmitted signal is supplied via detector 31 to frequency conversion mixer 34 and output is signal $b_2$.

If desired, measurements can be made through the fluid flowing in window 18 in the opposite direction by reversal of switch 22. In this case the input microwave signal is sampled by splitter 30 and supplied directly to frequency convertor 38 via extension 36 where it is converted to an output signal reference labelled $a_2$ in FIG. 2. In this instance the transmitted signal $b_1$ is supplied via detector 32 to mixer 33 and output as signal $b_1$. The reflected signal is supplied via circulator 27 to mixer 34 and output as signal $b_2$. Extensions 35 and 36 function in their respective switch positions of switch 22 to assure that reference signals $a_1$ and $a_2$ travel the same electrical path lengths in the S-parameter measurement circuit as do reflected and attenuated transmitted signals $b_1$ and $b_2$ so that phase relationships among these signals are maintained by the measurement circuit of FIG. 2.

A voltage tuned oscillator 40 and a harmonic generator 39 of conventional design supply mixers 33, 34, 37 and 38 with signals at a frequency appropriate to mix with input signals on their respective input lines and to convert these down to output frequencies (or DC if desired) for outputs $a_1$, $a_2$, $b_1$ and $b_2$. These output signals are used to form the ratios defining the S-Parameters are given below in Equations 1–4.

$$S_{21} = b_2/a_1 \quad (1)$$

$$S_{11} = b_1/a_1 \quad (2)$$

$$S_{22} = b_2/a_2 \quad (3)$$

$$S_{12} = b_1/a_2 \quad (4)$$

For the type of fixture used in these measurements it may be shown that these S-Parameters can be expressed in terms of the transmission coefficient T and the reflection coefficient $\Gamma$ as given in Equations 5 and 6 below:

$$S_{11} = \frac{(1-T^2)\Gamma}{1-T^2\Gamma^2} \quad (5)$$

$$S_{21} = \frac{(1-\Gamma^2)T}{1-T^2\Gamma^2} \quad (6)$$

If the parameter K is defined as in Equation 7:

$$K = \frac{S_{11}^2 - S_{21}^2 + 1}{2S_{11}} \quad (7)$$

then it can be shown that $\Gamma$ and T can be expressed as given in Equations 8 and 9 below:

$$\Gamma = K \mp (K^2 - 1)^{1/2} \quad (8)$$

$$T = \frac{S_{11} + S_{21} - \Gamma}{1 - (S_{11} + S_{21})\Gamma} \quad (9)$$

Given the transmission coefficient T and the reflection coefficient $\Gamma$ as determined from the solution to equations 8 and 9 by the programmed computer of FIG. 1, then the wave number $\kappa_u$ of the material between antennae 25 and 26 can be determined either as a function of T and $\Gamma$ or n (the phase shift parameter). In other words computer 16 can be programmed to compute $\kappa_u$ as a function of $\Gamma$ as in equation 10.

$$\kappa_u = \kappa_u(\Gamma) \quad (10)$$

or as a function of T and n as in equation 11.

$$\kappa_u = \kappa_u(T,n) \quad (11)$$

For a sample thickness d, and a phase shift integer, n, $$T = e^{-i\kappa_u d}$$

or $$i(ln(T) + i \, n \, 2\pi) = \kappa_u d \quad (13)$$

where e is the Napierian logarithm base and $i = (-1)^{1/2}$. It has been found that less error occurs in the determination of $\kappa_u$ if it is found as a function of T and n rather than $\Gamma$ alone.

Now $\Gamma$ and T can be used to determine n and then T and n used to determine $\kappa_u$ as given in equation 14 and 15 below:

$$-\pi\{[d\cdot\kappa_u(\Gamma) - i \, ln(T)]/2\pi + \tfrac{1}{2}\} \quad (14)$$

where n is truncated to the next lowest integer if the values of d, $\Gamma$, and T give the value in brackets { } as a non-integer. Once n is determined unambiguously in this way in the programmed computer 16, then the computer 16 is programmed to determine $\kappa_u$ from n and T as given in equation 15:

$$\kappa_u = (i \, ln(T) - 2\pi n)/d \quad (15)$$

The value of $\kappa_u$ so determined is, of course a complex number. In a wave guide of width $\omega$ $$\kappa_u = 2\pi \left\{ \frac{\epsilon_u}{\lambda_o^2} - \frac{1}{(2\omega)^2} \right\} \quad (16)$$

where $\lambda o$ is the free space wavelength of the incident microwave radiation and $\epsilon_u$ is the dielectric constant of the unknown fluid of wave number $\kappa_u$ in the waveguide. If the water cut fraction of the unknown fluid is expressed as f and $\epsilon o$ is the free space dielectric constant and $\epsilon \omega$ is the dielectric constant of the waveguide, then Hannai's equation states that the water fraction f or watercut is given by equation 17 as $$0 = \left(f - 1 + \frac{\epsilon - \epsilon_\omega}{\epsilon_o - \epsilon_\omega}\left(\frac{\epsilon_o}{\epsilon_\omega}\right)^{1/3}\right)\left(f - \frac{\epsilon - \epsilon_o}{\epsilon_\omega - \epsilon_o}\left(\frac{\epsilon_\omega}{\epsilon}\right)^{1/3}\right) \quad (17)$$

Now it will be noted that equation 17 is quadratic in f and thus two complex solutions are possible. If the measurements are accurate, one root should be pure real (to within the accuracy of the measurement) and the other will not. The pure real root of equation 17 will be the correct solution and the computer 16 is programmed to make this choice as the correct water cut f.

Thus the output computer 16 of FIG. 1 may be programmed appropriately to determine directly from the S-parameters as measured above, the water cut and other dielectric properties of the unknown production fluid.

The foregoing description may make other alternative embodiments of the invention apparent to those of skill in the art. It is the aim of the appended claims to cover all such alternative embodiments that fall within the true spirit and scope of the invention.

We claim:

1. A method for measuring the water fraction of a flowing multi-phase fluid having a water phase and an oil phase directly comprising the steps of:

flowing an unknown multiphase fluid through a test cell having known geometry and a window substantially transparent to microwave frequency electromagnetic energy;

continuously irradiating said test cell window with microwave energy and repetitively measuring microwave energy transmitted through said test cell and reflected from said test cell;

determining from said measured transmitted and reflected microwave energy the wave number $\kappa_u$ of the unknown multiphase fluid; and determining from said wave number and the known geometry of said test cell directly, the water fraction f of said unknown multiphase fluid.

2. The method of claim 1 wherein the step of determining the wave number $\kappa_u$ of the unknown multiphase fluid includes the step of determining from said measured transmitted and reflected microwave energy the $S_{11}$ and $S_{21}$ parameters defined as $$S_{11} = b_1/a_1$$

$$S_{21} = b_2/a_1$$

where $a^1$ is a reference amplitude of incident microwave energy, $b_1$, is the amplitude of the measured reflected microwave energy and b2 is the amplitude of the measured transmitted microwave energy.

3. The method of claim 2 wherein the step of determining the wave number $\kappa_u$ of the unknown multiphase fluid further includes the step of determining the parameter K from the $S_{11}$ and $S_{21}$ parameters where:

$$K = \frac{S_{11}^2 - S_{21}^2 + 1}{2S_{11}}$$

4. The method of claim 3 wherein the step of determining the wave number $\kappa_u$ of the unknown multiphase fluid further includes the step of determining from the parameters $S_{11}$, $S_{21}$ and K, the reflection coefficient $\Gamma$ and the transmission coefficient T of the unknown multiphase fluid where:

$$\Gamma = K \pm (K^2 - 1)^{1/2}$$

and $$T = \frac{S_{11} + S_{21}\Gamma}{1 - (S_{11} + S_{21})\Gamma}$$

5. The method of claim 4 wherein $\kappa_u$ is determined from T and n, where n is the phase shift integer defined by $$\kappa_u \cdot d = i(ln(T) + i\, n\, 2\pi)$$

where d is the thickness of the multiphase fluid flowing test cell, $i = (-1)^{1/2}$ and $\pi = 3.14159$.

6. The method of claim 1 wherein the measurements of reflected and transmitted microwave energy are performed at a microwave frequency in the range of 10 gigahertz and are fundamentally continuous wave measurements at this frequency range.

7. The method of claim 6 wherein said continuous wave measurements are performed repetitively.

8. The method of claim 7 wherein said continuous wave measurements are performed repetitively several hundred times per second.

9. The method of claim 8 wherein all of the steps are performed alternately with said irradiating and measuring said transmitted and reflected microwave energy first in one direction through said test cell and then in the opposite direction through said test cell.

10. The method of claim 1 wherein the steps are performed alternately with said in irradiating and measuring transmitted and reflected microwave energy is performed first in one direction through said test cell and then in the opposite direction through said test cell.

* * * * *